United States Patent
Forsline

(10) Patent No.: US 6,319,004 B1
(45) Date of Patent: Nov. 20, 2001

(54) HANDHELD DENTAL TOOL WITH A REMOVABLE SILICONE TIP

(75) Inventor: Ladd B. Forsline, Kutztown, PA (US)

(73) Assignee: Royal Sovereign Ltd. (GB)

( * ) Notice: Subject to any disclaimer, the term of this patent is extended or adjusted under 35 U.S.C. 154(b) by 0 days.

(21) Appl. No.: 09/629,583

(22) Filed: Jul. 31, 2000

(51) Int. Cl.$^7$ .................................................. A61C 3/00
(52) U.S. Cl. ............................................ 433/147; 433/11
(58) Field of Search .................................. 433/141, 142, 433/143, 146

(56) References Cited

U.S. PATENT DOCUMENTS

| | | |
|---|---|---|
| 532,720 | 1/1895 | Dennis . |
| 1,397,395 | 11/1921 | Bixler . |
| 1,586,302 | 5/1926 | Funk . |
| 2,016,597 | 10/1935 | Drake . |
| 2,099,030 | 11/1937 | Morrison . |
| 2,147,310 | 2/1939 | Morrison . |
| 3,869,797 | 3/1975 | Malmin . |
| 3,897,603 | 8/1975 | Brennenstuhl ........................ 15/150 |
| 4,060,897 * | 12/1977 | Greenstein ........................... 433/141 |
| 4,109,384 | 8/1978 | Dorian . |
| 4,206,547 * | 6/1980 | Tanaka ................................ 433/141 |
| 4,586,901 | 5/1986 | Tanaka et al. ...................... 433/164 |
| 5,100,321 | 3/1992 | Coss et al. ......................... 433/118 |
| 5,342,284 | 8/1994 | Lemon et al. ...................... 601/141 |
| 5,542,144 | 8/1996 | Forsline ............................ 15/245.1 |
| 5,899,693 | 5/1999 | Himeno et al. ..................... 433/119 |

OTHER PUBLICATIONS

*Standard Test Method for Static and Kinetic Coefficients of Friction of Plastic Film and Sheeting*, An American National Standard, Designation: D 1894—95$^{61}$; 5 pp.; 1995.

* cited by examiner

*Primary Examiner*—Cary E. O'Connor
(74) *Attorney, Agent, or Firm*—Patterson, Thuente, Skaar & Christensen, P.A.

(57) ABSTRACT

A handheld dental tool has a removable silicone tip. The tool includes a handheld shaft having at least one working end. The working end preferably includes a shoulder defined on the working end of the shaft and a spade member extending from the shoulder. The spade member has a longitudinal axis along a length of the spade member that has a generally uniform aspect ratio perpendicular to the longitudinal axis of between 2:1 and 4:1. A tip member comprised of a resilient silicone material that is removably mounted on the spade member. The tip member has a longitudinal axis along a length of the silicone tip and a cavity defined in a rear end of the silicone tip along the longitudinal axis. The cavity is adapted to receive the length of the spade member. The ratio of the length of the silicone tip member to the length of the spade member is greater than 1:1 and less than 2:1. Preferably, the surface of the spade member is smooth and the tip member slides on to and off of the spade member. The combination of the length of the spade member relative to the length of the silicone tip member and the coefficient of friction between the spade member and the silicone tip member create sufficient force to prevent the silicone tip from being pulled off of the spade member during normal use, but allow the silicone tip member to be manually removed in order to change tips or clean the tool.

20 Claims, 3 Drawing Sheets

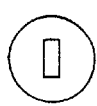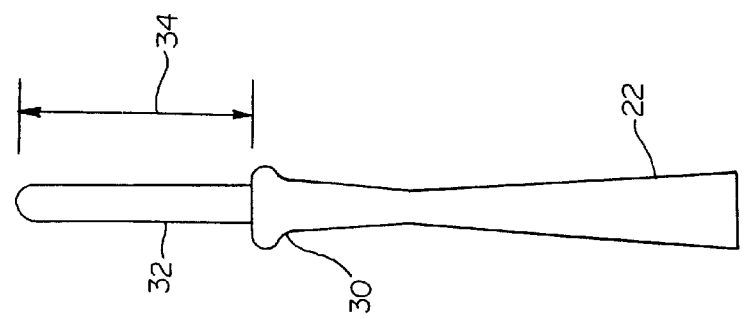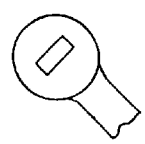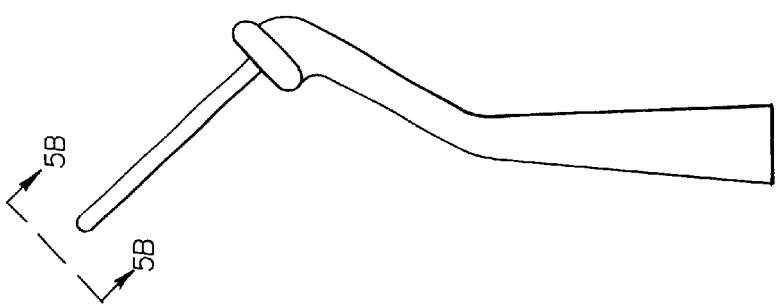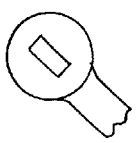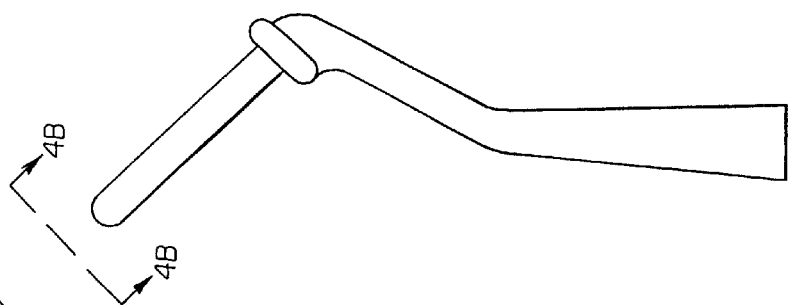

*Fig. 7A*  *Fig. 7B*
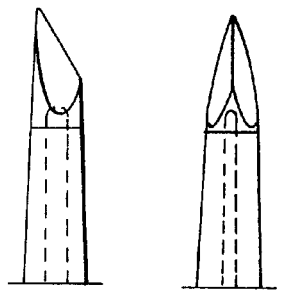
*Fig. 8A*  *Fig. 8B*  *Fig. 9A*  *Fig. 9B*
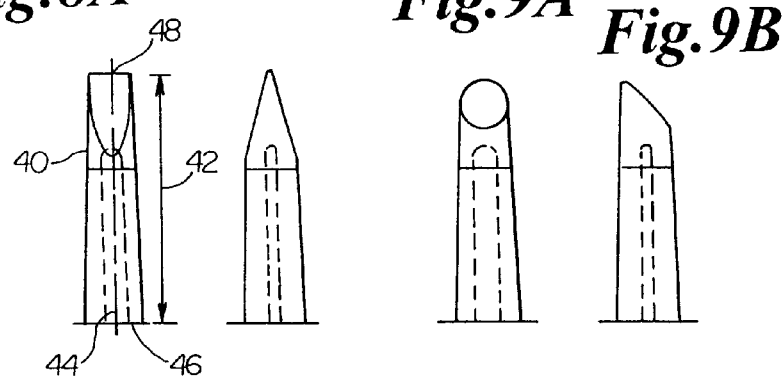
*Fig. 10A*  *Fig. 10B*  *Fig. 11A*  *Fig. 11B*
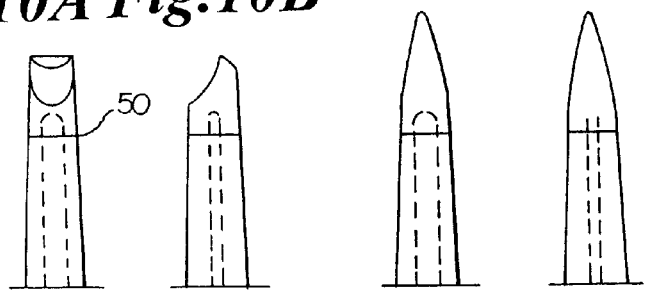

HANDHELD DENTAL TOOL WITH A REMOVABLE SILICONE TIP

FIELD OF THE INVENTION

The present invention relates generally to the field of dental tools and equipment. More specifically, the present invention relates to a handheld dental tool having a removable silicone tip.

BACKGROUND OF THE INVENTION

The use of various handheld tools is well known in the field of dentistry. One of the most common handheld dental tools is an explorer that typically consists of a metal shaft having a sharpened point at one or both ends of the shaft. U.S. Pat. Nos. 1,397.395 and 4,109,384 describe explorer-like dental tools that incorporate a flattened shank member as the working tip of the tool. In U.S. Pat. No. 1,397,395 the shank is integral to the handle, whereas in U.S. Pat. No. 4,109,384 the shank is secured in an end of the handle.

Another common handheld dental tool consists of a metal shaft having a pliable tip at one or both ends that is removable. U.S. Pat. Nos. 2,106,597 and 4,586,901 describe dental tools with removable tips where the tips are secured by a knob-like or button-like head at the distal end of the shaft. U.S. Pat. No. 532,720 describes a dental tool having a tip shaped similar to the shape of a pliable rubber shoe mounted over the tip where the shoe is either cylindrical or spoon-shaped. U.S. Pat. No. 5,342,283 describes a dental tool having a removable tip comprised of many soft flexible fibers. A knurled surface is used to mate the removable tip to this dental tool. U.S. Pat. Nos. 1,586,302 and 3,869,797 describe dental tools with removable tips mounted on cone-shaped shanks that include additional features such as the ability to carry a medicant or a magnetically activated instrument-carrying member.

U.S. Pat. Nos. 5,100,321 and 5,899,693 describe ultrasonic dental tools with removable tips mounted on cylindrical shafts. In U.S. Pat. No. 5,100,321, the indentation in the tip is round with a 3 degree converging, angle and has a length that is a little less than half the length of the tip. In U.S. Pat. No. 5,899,693 the connecting portion of the tip has an indentation with a diameter slightly smaller than the diameter of the distal shaft and the dimension are selected to maximize the transmission efficiency of the ultrasound energy.

Although dental tools having removable tips are well known, the pliable tips for such dental tools are typically made of a conventional rubber or plastic material. The use of a high-grade silicone material as the working tip for an artist paintbrush has been described in U.S. Pat. No. 5,542,144. In the preferred embodiment described in this patent, the silicone tip is held within a ferrule that is attached to the handle of the brush and a mechanism for expanding the tip against the side wall of the ferrule is used to aid in holding the tip within ferrule. In an alternate embodiment, the possibility of interchangeability of tips is described by using a female threaded ferrule and a male threaded handle. In this embodiment, it is preferred to use barbs or flutes extending from an insert positioned within the end of the tip to secure the tip to the ferrule and prevent the tip from rotating within the ferrule.

Other paint brushes have been developed which use a resilient working tip attached to a handle. In U.S. Pat. No. 2,147,310, a rubber tip is press fit into a ferrule or clamp that is attached to the handle. In U.S. Pat. No. 2,099,030, a spatula-like arrangement for a paint brush is described in which a round core extends from the distal end of the wooden shaft into a cavity in the back of the rubber tip. The cavity in the tip extends less than one-half the length of the tip. In an alternate embodiment, a rectangular shaped stepped extension is used in place of the round core. The purpose of this stepped extension is to create a shoulder that prevents the tip from riding up into the ferrule during operation. The rectangular shape is shown as having a ratio of width to height of 4 to 1. U.S. Pat. No. 4,897,603 describes a paintbrush having a spongy foam tip in the form of an envelope that is held in place on handle by a clamping arrangement. In one embodiment, a flat metal blade member extends into the center of the foam tip in order to provide additional stiffness to the working portion of the foam tip.

While it would be possible to use a paintbrush-like tool for dental applications, most of the working tips for paintbrushes are too large to easily make use of them in dental applications. More importantly, dental tools are preferably sterilized, and the ferrule or clamping arrangements used by these paintbrushes are not well suited for sterilization.

It would be desirable to provide a handheld dental tool having a working tip made of high-grade silicone material. Although existing techniques for attaching a pliable tip to a handheld dental tool could be utilized, the unique characteristics of high-grade silicone material present additional challenges in designing a versatile and functional handheld dental tool that incorporates a silicone tip.

SUMMARY OF THE INVENTION

The present invention is a handheld dental tool having a removable silicone tip. The tool includes a handheld shaft having at least one working end. The working end includes a shoulder defined on the working end of the shaft and a spade member extending from the shoulder. The spade member has a longitudinal axis along a length of the spade member that has a generally uniform aspect ratio perpendicular to the longitudinal axis of between 2:1 and 4:1. A tip member comprised of a resilient silicone material that is removably mounted on the spade member. The tip member has a longitudinal axis along a length of the silicone tip and a cavity defined in a rear end of the silicone tip along the longitudinal axis. The cavity is adapted to receive the length of the spade member. The ratio of the length of the silicone tip member to the length of the spade member is greater than 1:1 and less than 2:1.

Preferably, the shaft is made of a metal material and the shoulder and the spade member are formed of the metal material of the shaft. The surface of the spade member is smooth and the tip member slides on to and off of the spade member. The combination of the length of the spade member relative to the length of the silicone tip member and the coefficient of friction between the spade member and the silicone tip member create sufficient force to prevent the silicone tip from being pulled off of the spade member during normal use, but allow the silicone tip member to be manually removed in order to change tips or clean the tool. Preferably, the spade member is oversized relative to a size of the cavity by between 5% to 15% as a further way of insuring sufficient force to retain the silicone tip member during normal use.

In a preferred embodiment, a diameter of the rear end of the tip member is less than 5 mm. This small diameter does not lend itself to the conventional technique of using a knob or similar shouldered projection to removably attach the tip to the handle because the diameter of the knob required to effectively secure a silicone tip would be larger than 5 mm.

In this embodiment, the length of the spade member is between 7.5 mm and 15 mm and the width of the spade member is between 1 mm and 4 mm. The length of the tip member is between 10 mm and 25 mm. Preferably, the length of the spade member is about 12 mm and the width of the spade member is about 2 mm. The length of the tip member is about 16 mm. With this configuration, the present invention is able to adequately secure a removable silicone tip to a handheld dental tool using a spade member with a generally uniform cross-sectional area without the need for a knob or similar shouldered arrangement and without the use of a threaded ferrule arrangement as has been taught in the prior art.

In a preferred embodiment, the handheld dental tool is a double ended tool having working ends at both ends of the shaft. The working ends can be oriented relative to the longitudinal axis of the shaft anywhere between 0 degrees and 90 degrees. The orientation of the spade member at one working end can be oriented 90 degrees from an orientation of the spade member at the other working end, either in or out of a plane defined by the longitudinal axis. The orientation of the spade members may coincide with an orientation a working surface of the silicone tip member. Various shapes of the silicone tip member may be provided, including a flat chisel, an angel chisel, a cup chisel, a taper point or a cup round.

The handheld dental tool of the present invention can be used for a variety of dental procedures in either the dental lab or dental office, such as applying composite material to teeth and prosthetics, applying sterilizing and bonding gels, or for buildup of fluid-suspended porcelain. In the case of applying composite materials, the handheld dental tool the present invention dramatically improves over the performance of conventional titanium nitrade coated metal composite dental tools. Although the coating of these tools is meant be a nonstick surface, in practice composite materials will stick to the tools. The silicone tip of the present invention, on the other hand, exhibits significantly improved performance over such coated metal tools in this application as composite material does not stick to the silicone tip.

BRIEF DESCRIPTION OF THE DRAWINGS

FIGS. 4A and 4B are a detailed plan view and an end view of an alternate embodiment of one end of an angled double-ended handheld dental tool.

FIGS. 5A and 5B are a detailed plan view and an end view of the other end of the angled double-ended handheld dental tool shown in FIGS. 4A and 4B.

FIGS. 6A and 6B are a detailed plan view and an end view of a straight end of a single-ended handheld dental tool.

FIGS. 7A and 7B through FIGS. 11A and 11B are cut-away plan views of various embodiments of the removable tips in accordance with the present invention.

DETAILED DESCRIPTION OF THE PREFERRED EMBODIMENT

Figure 1:
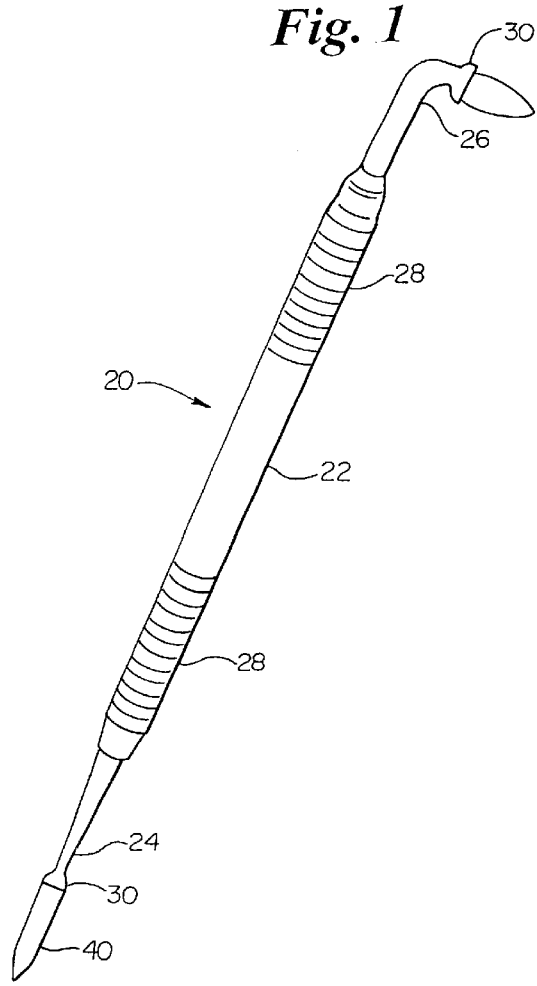
FIG. 1 is an isometric view of one embodiment of a double-ended handheld dental tool in accordance with the present invention featuring a straight end and a right-angle end.
Figure 2:
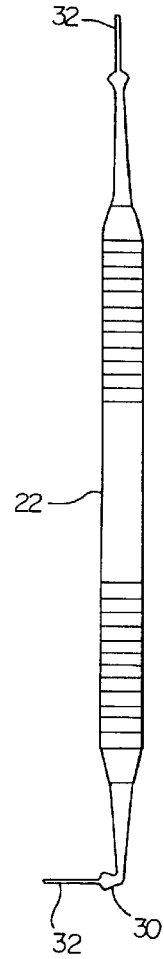
FIGS. 2 and 3 are plan views of the dental tool of FIG. 1.
Figure 3:
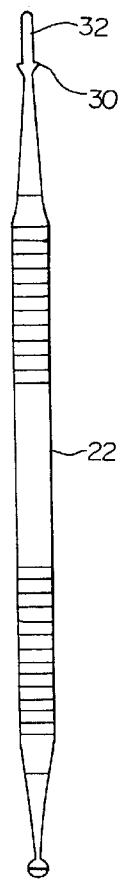

Referring to FIGS. 1–3, a handheld dental tool 20 in accordance with one embodiment of the present invention will be described. The tool 20 includes a handheld shaft 22 having at least one working end 24, 26. The working end 24, 26 preferably includes a shoulder 30 defined on the working end 24, 26 and a spade member 32 extending from the shoulder 30. As shown best in FIGS. 4–6, the spade member 32 has a longitudinal axis 34 along a length of the spade member that preferably has a generally uniform aspect ratio perpendicular to the longitudinal axis of between 2:1 and 4:1. A tip member 40 is comprised of a resilient silicone material and is adapted to be removably mounted on the spade member 32. The preferred range of aspect ratio of the spade member avoids wasting material, yet prevents any rotation of the tip member 40 about the spade member 32. As shown best in FIGS. 7–11 the tip member 40 has a longitudinal axis 42 along a length of the silicone tip and a cavity 44 defined in a rear end 46 of the silicone tip 40 along the longitudinal axis. The cavity 44 is adapted to receive the length of the spade member 32. The ratio of the length of the silicone tip member 40 to the length of the spade member 32 is greater than 1:1 and less than 2:1. When coupled with the coefficient of friction of the silicone material of the present invention, the range of lengths of the spade member 32 serves to firmly secure the tip member 40 on the spade member 32 without the need for a knob-like protrusion that would otherwise increase the overall diameter of the tip member 40.

Although a the tool 20 could be provided without a shoulder 30, the shoulder 30 serves several desirable functions in the preferred embodiment. In operation, the shoulder 30 serves as a physical and visual confirmation of how far the tip member 40 is inserted onto the spade member 32. The shoulder 30 also serves as a physical and visual confirmation to the operator of how the far the tool 20 is moved within the mouth, particularly the depth to which the tool may be inserted between teeth or in a cavity in the mouth.

Preferably, the shaft 22 is made of a metal material such as 410 stainless steel. In one embodiment, the shaft 22 includes a pair of knurled sections 28 to aid in gripping the shaft 22. The shoulder 30 and the spade member 32 are formed of the same metal material as the shaft 22. Alternatively, a plastic or composite material could also be utilized provided the material has sufficient strength and rigidity to perform as a handheld tool. Preferably, the surface of the spade member 32 is smooth. This enables the tip member 40 to slide on to and off of the spade member 32 when tension is manually applied in the direction parallel to the longitudinal axis of the spade member 32. Alternatively, surface features such as cross hatching or grooves may be applied to the surface of the spade member 32 to make it somewhat more difficult to remove the tip member 40. The combination of the length of the spade member 32 relative to the length of the silicone tip member 40 and the coefficient of friction between the spade member 32 and the silicone tip member 40 create sufficient force to prevent the silicone tip member 40 from being pulled off of the spade member 32 during normal use, but allow the silicone tip member 40 to be manually removed in order to change tips or clean the tool. Preferably, the spade member 40 is oversized relative to a size of the cavity 44 by between 5% to 15% as a further way of insuring sufficient force to retain the silicone tip member 40 during normal use.

In a preferred embodiment, a diameter of the rear end 46 of the tip member 40 is less than 5 mm. This small diameter does not lend itself to the conventional technique of using a knob or similar shouldered projection to removably attach the tip to the handle because the diameter of such a knob required to effectively secure a silicone tip to the handle would be larger than 5 mm. In this embodiment, the length of the spade member 32 is between 7.5 mm and 15 mm and the width of the spade member 32 is between 1 mm and 4 mm. The length of the tip member 40 is between 10 mm and 25 mm. Preferably, the length of the spade member 32 is about 12 mm and the width of the spade member 32 is about 2 mm. The length of the tip member 40 is about 16 mm.

In a preferred embodiment, the handheld dental tool 20 is a double ended tool having working ends 24, 26 at both ends of the shaft 22. The working ends 24, 26 can be oriented relative to the longitudinal axis of the shaft 22 anywhere between 0 degrees and 90 degrees. The orientation of the spade member 32 at one working 26 end can be oriented 90 degrees from an orientation of the spade member 32 at the other working end 24, either in or out of a plane defined by the longitudinal axis. The orientation of the spade members 32 may coincide with an orientation a working surface 48 of the silicone tip member 42.

As shown in FIGS. 7–11 various shapes of the silicone tip member may be provided, including a flat chisel, an angel chisel, a cup chisel, a taper point or a cup round. It can be seen in the use cutaway figures that the cavity 44 extends more than half of the length of the tip 40. In the embodiments shown in these figures, the deep working portion of the tip member 40 is that portion above the line shown at 50. As will be seen, when the tip member 40 is fully positioned on the spade member 32 a small portion of the spade member extends into the working portion 50 of the tip member 40. The line 50 denoting the working portion of the tip member 40 is shown at a depth of between 55 to 65 percent of the overall length of the tip member 40, depending upon the particular shape of the tip member. The portion of the cavity 44 extends beyond the line 50 represents an additional depth of between 5 to 10 percent of the overall length of the tip member 40.

Preferably the silicone material that comprises the tip member 40 is a commercial grade silicone cured using a platinum or peroxide catalyst, such as E4357 or a similar product available from American Silicones, Inc. In this embodiment, the silicone material has a coefficient of friction of between 0.3 and 0.5 and preferably between 0.3 and 0.4 as measure by the ANS Standard Test Method for Static and Kinetic Coefficients of Friction of Plastic Film and Sheeting. The durometer of the silicone material of the preferred embodiment is about 80, but may range from 40 to 85. The tear strength of the silicone material of the preferred embodiment is 225. The tear strength will vary as a function of durometer from 175 to more than 250. The specific gravity of the silicone material of the preferred embodiment is between 1.17 and 1.23 and may range between 1.10 and 1.25.

Although the preferred embodiment of the automated system of the present invention has been described, it will be recognized that numerous changes and variations can be made and that the scope of the present invention is to be defined by the claims.

What is claimed is:

1. A handheld dental tool comprising:
   a handheld shaft having at least one working end, the working end including a shoulder defined on the working end of the shaft and a spade member extending from the shoulder, the spade member having a longitudinal axis along a length of the spade member that has a generally uniform aspect ratio perpendicular to the longitudinal axis of between 2:1 and 4:1; and
   a tip member comprised of a resilient silicone material that is removably mounted on the spade member, the tip member having a longitudinal axis along a length of the silicone tip member and a cavity defined in a rear end of the silicone tip member along the longitudinal axis that is adapted to receive the length of the spade member wherein a ratio of the length of the silicone tip member to the length of the spade member is greater than 1:1 and less than 2:1.

2. The dental tool of claim 1 wherein the shaft is comprised of a metal material and the shoulder and the spade member are formed of the metal material of the shaft.

3. The dental tool of claim 1 wherein a surface of the spade member is smooth and the tip member slides on to the spade member.

4. The dental tool of claim 1 the spade member is oversized relative to a size of the cavity by between 5% to 15%.

5. The dental tool of claim 1 wherein the tip member has a generally cylindrical shape at the rear end and has a working end having a shape selected from the set comprising a flat chisel, an angel chisel, a cup chisel, a taper point or a cup round.

6. The dental tool of claim 1 wherein the length of the spade member is between 7.5 mm and 15 mm and a width of the spade member is between 1 mm and 4 mm and wherein the length of the tip member is between 10 mm and 25 mm.

7. The dental tool of claim 6 wherein the length of the spade member is about 12 mm and the width of the spade member is about 2 mm and wherein the length of the tip member is about 16 mm and a diameter of the rear end of the tip member is about 4 mm.

8. The dental tool of claim 1 wherein the longitudinal axis of the spade member defines an angle with a longitudinal axis of the handheld shaft of between 0 degrees and 90 degrees.

9. The dental tool of claim 1 wherein the handle has two working ends one at each end of the shaft.

10. The dental tool of claim 9 wherein an orientation of the spade member at one working end is oriented 90 degrees from an orientation of the spade member at the other working end.

11. The dental tool of claim 10 wherein the difference in the orientation of the spade members is in a plane defined by the longitudinal axis of the handle.

12. The dental tool of claim 10 wherein the difference in the orientation of the spade members is out of a plane defined by the longitudinal axis of the handle.

13. The dental tool of claim 1 wherein the silicone material is a commerical grade silicone cured using a platinum or peroxide catalyst.

14. The dental tool of claim 1 wherein the silicone material has a coefficient of friction of between 0.3 and 0.5.

15. A handheld dental tool comprising:
    a handheld shaft having at least one working end, the working end including a spade member extending from the working end and having a longitudinal axis along a length of the spade member and a generally uniform cross-sectional area along the length of the longitudinal axis; and
    a tip member comprised of a resilient silicone material that is removably mounted on the spade member, the tip member having a longitudinal axis along a length of the silicone tip member and a cavity defined in a rear end of the silicone tip member along the longitudinal axis that is adapted to receive the length of the spade member wherein a diameter of the rear end of the tip member is less than about 5 mm and a ratio of the length of the silicone tip member to the length of the spade member is greater than 1:1 and less than 2:1, such that a combination of the length of the spade member relative to the length of the silicone tip member and a coefficient of friction between the spade member and the silicone tip member create sufficient force to prevent the silicone tip member from being pulled off of the spade member during normal use, but allow the silicone tip member to be manually removed to change tip members or clean the tool.

16. The dental tool of claim 15 wherein the length of the spade member is between 7.5 mm and 15 mm and a width of the spade member is between 1 mm and 4 mm and wherein the length of the tip member is between 10 mm and 25 mm.

17. The dental tool of claim 16 wherein the length of the spade member is about 12 mm and the width of the spade member is about 2 mm and wherein the length of the tip member is about 16 mm and a diameter of the rear end of the tip member is about 4 mm.

18. The dental tool of claim 15 the spade member is oversized relative to a size of the cavity by between 5% to 15%.

19. The dental tool of claim 15 the silicone material is a commercial grade silicone material having a coefficient of friction of between 0.3 and 0.5, a durometer of between 40 and 85 and a tear strength of greater than 175.

20. The dental tool of claim 19 the silicone material has a coefficient of friction of between 0.3 and 0.5, a durometer of about 80 and a tear strength of about 220.

* * * * *

UNITED STATES PATENT AND TRADEMARK OFFICE
CERTIFICATE OF CORRECTION

PATENT NO. : 6,319,004 B1
DATED : November 20, 2001
INVENTOR(S) : Forsline

It is certified that error appears in the above-identified patent and that said Letters Patent is hereby corrected as shown below:

Column 1,
Line 15, "1,397.395" should be -- 1,397,395 --.
Line 44, "dimension" should be -- dimensions --.
Line 56, "within ferrule" should be -- within the ferrule --.

Column 2,
Line 11, "on handle" should be -- on the handle --.

Column 3,
Line 23, "orientation a working" should be -- orientation of a working --.
Line 32, "dental tool the" should be -- of --.
Line 36, "meant be" should be -- meant to be --.

Column 4,
Line 25, "Although a the" should be -- Although the --.
Line 31, "how the far" should be -- how far --.
Line 35, "as 410 stainless" should be -- as stainless --.

Column 5,
Line 11, "26 end" should be -- end 26 --.
Line 14, "members" should be -- member --.
Line 16, "7-11 various" should be -- 7-11, various --.
Line 26, "working portion 50 of" should be -- working portion of --.
Line 30, "extends" should be -- extending --.
Line 40, "measure" should be -- measured --.

Column 6,
Line 35, "ends one" should be -- ends one --.

UNITED STATES PATENT AND TRADEMARK OFFICE
CERTIFICATE OF CORRECTION

PATENT NO.   : 6,319,004 B1
DATED        : November 20, 2001
INVENTOR(S)  : Forsline It is certified that error appears in the above-identified patent and that said Letters Patent is hereby corrected as shown below:

Column 8,
Line 4, "claim 15 the" should be -- claim 15 wherein the --.
Line 7, "claim 15 the" should be -- claim 15 wherein the --.
Line 11, "claim 19 the" should be -- claim 19 wherein the --.

Signed and Sealed this

Twenty-seventh Day of August, 2002

Attest:

Attesting Officer

JAMES E. ROGAN
Director of the United States Patent and Trademark Office